United States Patent [19]

Bodor et al.

[11] 4,443,435

[45] Apr. 17, 1984

[54] PRODRUGS OF 6-MERCAPTOPURINE AND 6-MERCAPTOPURINE RIBOSIDES AND THERAPEUTIC COMPOSITIONS AND METHODS EMPLOYING THEM

[75] Inventors: Nicholas S. Bodor; Kenneth B. Sloan, both of Gainesville, Fla.; Stefano A. Pogany, Lawrence, Kans.

[73] Assignee: Merck & Co., Inc., Rahway, N.J.

[21] Appl. No.: 320,264

[22] Filed: Nov. 12, 1981

Related U.S. Application Data

[63] Continuation-in-part of Ser. No. 290,625, Aug. 3, 1981, abandoned, which is a continuation of Ser. No. 141,981, Apr. 21, 1980, abandoned.

[51] Int. Cl.³ .................... A61K 31/52; A61K 31/70; C07D 473/24
[52] U.S. Cl. .................................. 424/180; 424/248.5; 424/253; 424/251; 424/263; 424/273 R; 424/274; 424/311; 424/319; 536/24; 544/159; 544/276; 544/302; 544/314; 546/300; 546/301; 548/337; 548/533; 560/152; 562/556; 562/557
[58] Field of Search .................. 544/265, 276; 536/24; 424/180, 253

[56] References Cited

U.S. PATENT DOCUMENTS

| | | | |
|---|---|---|---|
| 2,844,576 | 7/1958 | Goldman et al. | 544/265 |
| 2,852,506 | 9/1958 | Goldman et al. | 544/265 |
| 3,915,958 | 10/1975 | Shuman et al. | 260/211.5 R |
| 3,957,803 | 5/1976 | Bodor et al. | 424/263 X |
| 4,061,753 | 12/1977 | Bodor et al. | 424/253 |
| 4,235,887 | 11/1980 | Voorhees et al. | 424/180 |
| 4,275,064 | 6/1981 | Bodor et al. | 424/253 |

FOREIGN PATENT DOCUMENTS

| | | | |
|---|---|---|---|
| 36145 | 9/1981 | European Pat. Off. | 424/253 |
| 38541 | 10/1981 | European Pat. Off. | 536/24 |
| 2010136 | 2/1970 | France | 424/253 |

OTHER PUBLICATIONS

"Chemical Aspects of Pro-drug Design", Papers presented at a meeting held in London on Nov. 14, 1979, Chemistry & Industry, No. 11, Jun. 7, 1980, pp. 433–456.
Furuno, et al., Chemical Abstracts, vol. 78, 93111k (1973).
Bioindustria SpA, Chemical Abstracts, vol. 85, 63084f (1976).
Tanikaga, et al., Chemical Abstracts, vol. 87, 22280q (1977).

*Primary Examiner*—Donald G. Daus
*Assistant Examiner*—Diana G. Rivers
*Attorney, Agent, or Firm*—Mario A. Monaco; Michael C. Sudol, Jr.

[57] ABSTRACT

Novel, transient prodrug forms of biologically active agents containing mercapto groups have (i) the structural formula (I):

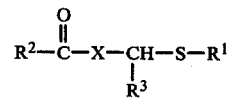

wherein
X is O, S, or $NR^5$;
$R^1S$ is the residue of any biologically active agent $R^1SH$;
$R^2$ is selected from the group consisting of straight or branched chain alkyl having from 1 to 20 carbon atoms; aryl having from 6 to 10 carbon atoms; cycloalkyl having from 3 to 8 carbon atoms; alkenyl having from 2 to 20 carbon atoms; cycloalkenyl having from 4 to 8 carbon atoms; alkynyl having from 2 to 20 carbon atoms; aralkyl, alkaryl, aralkenyl, aralkynyl, alkenylaryl, alkynylaryl, loweralkanoyloxyalkyl, carboxyalkyl, and lower alkanoyloxyalkyl wherein alkyl, aryl, alkenyl and alkynyl are as defined above; saturated or unsaturated monoheterocyclic or polyheterocyclic, or fused heterocyclic, either directly bonded to the carbonyl function or linked thereto via an alkylene bridge, containing from 1 to 3 of any one or more of the heteroatoms N, S or O in each heterocyclic ring thereof and each such ring being from 3- to 8- membered; and mono- or polysubstituted derivatives of the above, each of said substituents being selected from the group consisting of lower akyl, lower alkoxy, lower acyl, lower acyloxy, halo, haloloweralkyl, cyano, carbethoxy, loweralkylthio, amino, nitro, loweralkylamino, diloweralkylamino, carboxyl, carbamyl, loweralkylcarbamyl, diloweralkylcarbamyl and

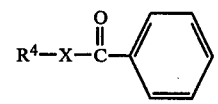

wherein
$R^4$ is hydrogen or alkyl having from 1 to 10 carbons;
$R^3$ is hydrogen, $R^2$, lower acyl, cyano, haloloweralkyl, carbamyl, loweralkylcarbamyl, diloweralkylcarbamyl, $-CH_2ONO_2$ and $-CH_2OCOR^2$;
$R^5$ is hydrogen or lower alkyl; and further wherein
$R^2$ and $R^3$ may be taken together to form a cyclizing moiety selected from the group consisting of

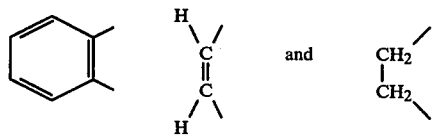

with the proviso that when $R^1S$ is the residue of a sulfur containing amino acid, then X cannot be $NR^5$;
(ii) the structural formula (I) wherein

is the residue of any naturally occurring protein amino acid, the residue of any N-substituted naturally occurring amino acid, which N-substituent is lower alkyl or any amino acid protective group cleavable via hydrogenolysis or hydrolysis, or the residue of an N,N-lower dialkyl of $C_4$–$C_7$ cycloalkylamino acid; and (iii) the non-toxic, pharmaceutically acceptable salts thereof.

12 Claims, No Drawings

PRODRUGS OF 6-MERCAPTOPURINE AND 6-MERCAPTOPURINE RIBOSIDES AND THERAPEUTIC COMPOSITIONS AND METHODS EMPLOYING THEM

RELATED APPLICATION

This application is a continuation-in-part of co-pending application Ser. No. 290,625 filed Aug. 3, 1981 which in turn is a continuation of application Ser. No. 141,981 filed Apr. 21, 1980, both now abandoned.

BACKGROUND OF THE INVENTION

1. Field of the Invention

The present invention relates to novel, transient prodrug derivatives of the biologically active compounds which contain a mercapto moiety, and, more especially, relates to certain acyl-X-methylthioether latentiated forms of such thio compounds.

As employed in this application, the expression "prodrug" denotes a derivative of a known and proven prior art compound, which derivative, when absorbed into the bloodstream of a warm-blooded animal, "cleaves" in such a manner as to release the proven drug form and permits the same to attain a higher bioavailability level than that which could be obtained if the proven drug form, per se, was administered.

Furthermore, also as used in this application, the term "transient" denotes "cleavage" of the compounds of this invention in such a manner that the proven drug form is released and the remaining "cleaved" moiety is non-toxic and metabolized in such a manner that non-toxic, metabolic products are produced.

2. Description of the Prior Art

It is well known to this art that the biologically active compounds which contain a mercapto group (—SH) and their salts, e.g., cysteine, cysteine methyl ester, N-acetylcysteine, penicillamine, dimercaprol, thiopental, 2-mercaptopyridine N-oxide, methimazole, propylthiouracil, N-(2-methyl-3-thio-propionyl)proline, 2-thiouracil, 6-mercaptopurine, glutathione, 6-thioguanine, 6-thioguanosine, 6-mercaptopurineriboside, as well as corresponding protected ester derivatives and salts are useful active agents for the treatment or management of a wide variety of disease states or conditions, e.g., cancer, psoriasis, hypertension, fungal infections, hyperthyroidism, metal poisoning, excess mucus, pain (general anesthesia).

Nevertheless, it too is well known to the art that such mercapto containing compounds, and the various art-recognized therapeutically active derivatives thereof, are characterized by certain inherent disadvantages, notably serious bioavailability and physiological availability problems upon administration. Such reduced availability can be attributed in part to poor lipid solubility [by reason of the presence of the hydrophilic mercapto group], and also to metabolic losses during and following conventional administration. Other disadvantages associated with the prior art compounds are instability to both air and light, and same are subject to chemical attack by many agents that are conventionally used in pharmaceutical preparations, as well as a variety of other unfavorable pharmacodynamic properties.

Thus, there exists a clear and present need for novel latentiated forms of biologically active substances containing mercapto moieties which derivatives would be devoid of those disadvantages and drawbacks that to date have characterized the prior art compounds.

SUMMARY OF THE INVENTION

Accordingly, a major object of the present invention is the provision of a novel class of prodrugs of biologically active compounds which contain mercapto groups.

Another object of this invention is the provision of a novel class of mercapto compound prodrugs that is essentially free from the unwanted effects associated with the prior art.

Still another object of the invention is to provide a new and useful class of latentiated mercapto compounds which is characterized by enhanced stability and solubility, can be administered in standard pharmaceutical formulations to warm-blooded animals to elicit a local, topical or systemic physiological or pharmacological beneficial effect, and which exhibits enhanced bioavailability and physiological availability.

Yet another object is to provide a novel class of prodrugs of biologically active compounds which contain mercapto groups which will elicit a more effective therapeutic response, at lower concentrations or dosage levels, than its parent molecules.

Other objects, features and advantages of the invention will be apparent to those skilled in the art from the detailed description of the invention which follows.

DETAILED DESCRIPTION OF THE INVENTION

More particularly according to this invention, all of the aforenoted objects, features and advantages thereof are provided by the novel prodrugs of biologically active mercaptan containing compounds (i) having the structural formula (I):

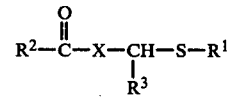

wherein
X is O, S or NR$^5$;
R$^1$ is the deprotonated residue of a biologically active agent R$^1$SH such as
  (a) thiopurine, especially 6-mercaptopurine or 6-mercaptopurine riboside;
  (b) 6-thioguanosine;
  (c) thiopental;
  (d) N-(2-methyl-3-thiopropionyl)proline or an ester or amide thereof;
  (e) N-acetyl cysteine;
  (f) cysteine methyl ester;
  (g) dimercaprol;
  (h) penicillamine;
  (i) glutathione;
  (j) 2-thiopyridine-N-oxide;
  (k) 2-thiouracil;
  (l) 6-thioguanine; or
  (m) methimazole;
R$^2$ is
  (a) straight or branched chain alkyl having from 1 to 20 carbon atoms especially methyl, ethyl, isopropyl, t-butyl, pentyl or hexyl;
  (b) aryl having from 6 to 10 carbon atoms especially phenyl, substituted penyl or naphthalene;

(c) cycloalkyl having from 3 to 8 carbon atoms especially cyclopentyl, or cyclohexyl;

(d) alkenyl having from 2-20 carbon atoms especially $C_{2-6}$ alkenyl such as vinyl, allyl, or butenyl;

(e) cycloalkenyl having from 5 to 8 carbon atoms especially cyclopentenyl or cyclohexenyl;

(f) alkynyl having from 2 to 20 carbon atoms especially $C_{2-6}$ alkynyl for example, ethynyl, propynyl or hexynyl;

(g) aralkyl, alkaryl, aralkenyl, aralkynyl, alkenylaryl or alkynylaryl wherein alkyl, aryl, alkenyl and alkynyl are as previously defined;

(h) loweralkoxycarbonyl especially $C_{1-6}$ alkoxycarbonyl such as methoxycarbonyl, ethoxycarbonyl, t-butoxycarbonyl and cyclopentoxycarbonyl;

(i) carboxyalkyl or alkanoyloxyalkyl especially carboxy-$C_{1-6}$alkyl such as formyloxymethyl and formyloxypropyl; or $C_{1-6}$(alkylcarboxyalkyl) such as acetoxymethyl, n-propanoyloxyethyl and pentanoyloxybutyl;

(j) saturated or unsaturated monoheterocyclic or polyheterocyclic, or fused heterocyclic, either directly bonded to the carbonyl function or linked thereto via an alkylene bridge, containing from 1 to 3 of any one or more of the heteroatoms N, S or O in each heterocyclic ring thereof and each such ring being from 3- to 8-membered; and (k) mono- or polysubstituted derivatives of the above, each of said substituents being selected from the group consisting of lower alkyl; lower alkoxy; lower alkanoyl; lower alkanoyloxy; halo especially bromo, chloro, or fluoro; haloloweralkyl especially fluoro, chloro or bromoloweralkyl such as trifluoromethyl and 1-chloropropyl; cyano; carbethoxy; loweralkylthio, especially $C_{1-6}$ loweralkylthio such as methylthio, ethylthio and n-propylthio; nitro; carboxyl; amino; loweralkylamino especially $C_{1-6}$ alkylamino, for example, methylamino, ethylamino and n-butylamino; diloweralkylamino especially di($C_{1-6}$loweralkyl)amino such as N,N-dimethylamino, N,N-diethylamino and N,N-dihexylamino; carbamyl; loweralkylcarbamyl especially $C_{1-6}$alkylcarbamyl such as methylcarbamyl and ethyl carbamoyl; and

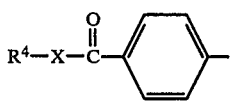

wherein $R^4$ is hydrogen or alkyl having from 1 to 10 carbons;
$R^3$ is
(a) hydrogen;
(b) $R^2$;
(c) lower alkanoyl;
(d) cyano;
(e) haloloweralkyl;
(f) carbamyl, loweralkylcarbamyl, or diloweralkylcarbamyl;
(g) —$CH_2ONO_2$; or
(h) —$CH_2OCOR^2$;
$R^5$ is hydrogen or lower alkyl; and further wherein $R^2$ and $R^3$ may be taken together to form a ring cyclizing moiety selected from th group consisting of:

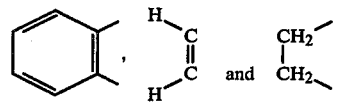

e.g., to form compounds of the type:

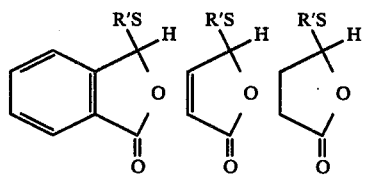

with the proviso that when $R^1S$ is the residue of a sulfur containing amino acid, then X cannot be $NR^5$;

(ii) prodrugs having the structural formula (I) wherein

is the residue of any naturally occurring protein amino acid, the residue of any N-substituted naturally occurring amino acid, which N-substituent is lower alkyl or any amino acid protective group cleavable via hydrogenolysis or hydrolysis (e.g., formyl, benzyloxy, carbonyl, t-butyloxycarbonyl), or the residue of an N,N-lower-dialkyl or $C_4$–$C_7$ cycloalkylamino acid; and (iii) the non-toxic, pharmaceutically acceptable salts thereof.

The term "naturally occurring protein amino acid" includes without limitation:

| | |
|---|---|
| Glycine | Arginine |
| Alanine | Lysine |
| Valine | Hydroxylsine |
| Leucine | Phenylalanine |
| Isoleucine | Tyrosine |
| Cysteine | Asparagine |
| Cystine | Glutamine |
| Methionine | Proline |
| Serine | Hydroxyproline |
| Threonine | Histidine |
| Aspartic acid | Tryptophan |
| Glutamic acid | Pyroglutamic acid |

Similarly, the import of the phrase "amino acid protective group 'cleavable' via hydrogenolysis or hydrolysis" can be further gained fom a review of U.S. Pat. No. 3,803,102 to Felix and U.S. Pat. No. 3,957,803 to Bodor, et al.

It too will be appreciated that by "residue" of a naturally occurring amino acid there are intended not only those species wherein the "CO" of the $R^2$—CO— moiety comprising the topic prodrugs is the carbonyl function originating from the amino acid, per se, e.g., species of type

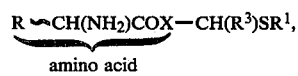

amino acid but also such species including a free carboxyl function, e.g., species of the type

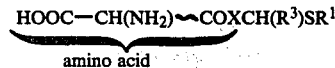

as well as amino acid species of amido type, wherein the —CONHR⁵ function comprises the parent amino acid, e.g., species of the type

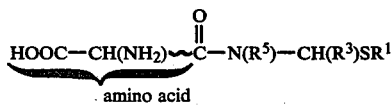

When $R^2$ comprises a heterocyclic function, representative such heterocycles include, without limitation, and without regard to the point of attachment on the ring, piperazinyl, 4-methylpiperazinyl, pyridinyl, pyrazinyl, pyrimidinyl, pyridazinyl, pyrazolyl, pyrrolyl, pyrrolidinyl, pyrrolinyl, pyrazolinyl, pyrazolidinyl, piperidyl, morpholinyl, quinuclidinyl, isoindolinyl, indolinyl, thienyl, benzothienyl, napthothienyl, thianthrenyl, furyl, pyranyl, chromenyl, xanthenyl, phenoxathiinyl, imidazolyl, pyridyl, indolizinyl, isoindolyl, 3H-indolyl, indolyl, indazolyl, purinyl, phthalazinyl, quinolyl, isoquinolyl, 4-uinolizinyl, quinoxalinyl, naphthyridinyl, cinnolinyl, pteridinyl, carbazolyl, 4aH-carbazolyl, β-carbolinyl, phenanthridinyl, acridinyl, perimidinyl, phenoxazinyl, furazanyl, isochromanyl, chromanyl, imidazolinyl, 1-methyl-azarinyl, 1-methyl-pyrrolyl, 1-methyl-imidazolyl, 1-methyl-pyrazolyl, 2-methyl-isoindolyl, 3H-indolyl, phtalazinyl, quinoxilinyl, quinazidinyl, phenazinyl, isothiazolyl, 10-methylphenothiazinyl, isoxazolyl, furazanyl, the various saturated, unsaturated or partially saturated congeners of any of the above, and those attached to the carbonyl carbon via a lower alkylene bridge.

Even though $R^1S$— has been defined as the residue from any biologically active compound, $R^1SH$, the scope of this invention is not meant to be limited to these parent compounds. It should be obvious to one skilled in the arts that simple derivatives of certain functional groups which are attached to $R^1$ would also fall under the definition of $R^1$, e.g., acyl derivatives of hydroxyl and amino moieties, ester and amide derivatives of carboxylic acids or other standard protecting groups which could be easily utilized.

Likewise when an acidic or basic moiety is a part of $R^1$, pharmaceutically acceptable salts thereof would also be a part of this invention.

By "pharmaceutically acceptable salt," there are intended the conventional non-toxic salts or the quaternary ammonium salts of the compounds of the formula (I), formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, toluenesulfonic, and the like.

The pharmaceutically acceptable salts of the present invention can be synthesized from the compounds embraced by formula (I) which contain a basic or acidic moiety by conventional chemical methods. Generally, the salts are prepared by reacting the free base or acid with stoichiometric amounts or with an excess of the desired salt forming inorganic or organic acid or base in a suitable solvent or various combination of solvents. For example, the free base can be dissolved in a mixed aqueous solution of the appropriate acid and the salt recovered by standard techniques, for example, by evaporation of the solution. Alternatively, the free base can be charged into an organic solvent such as a lower alkanol, a symmetrical or asymmetrical ether containing 2 to 10 carbon atoms, an alkyl ester, or mixtures thereof, and the like, and then it is treated with the appropriate acid to form the corresponding salt. The salt is recovered by standard recovery techniques, for example, by filtration of the desired salt or spontaneous separation from the solution, or it can be precipitated by the addition of a solvent in which the salt is insoluble and recovered therefrom.

Examples of suitable inorganic and organic solvents for performing the various reactions include any inorganic or organic solvent that does not adversely affect the reactants or the resulting product, including halogenated solvents such as methylene chloride, chloroform, carbon tetrachloride, ethylene chloride, ether solvents such as tetrahydrofuran, dioxane, diglyme, n-hexane, cyclooctane, benzene, heptane, cyclohexane; mixtures thereof, and like aliphatic, cylcoaliphatic and aromatic hydrocarbon solvents, water, acidified aqueous solutions, mixed organic and inorganic solutions, ethyl acetate, propyl acetate, and the like.

The "quaternary ammonium salts" are likewise conventional to the pharmaceutical arts, and these too are prepared via typical methodology. Moreover, either the $R^1$ or the $R^2$ moiety, or both, of the subject prodrug molecules can be quaternized or otherwise comprise a salt function.

The compounds of the present invention are conveniently prepared via the following general syntheses:

SYNTHETIC SCHEME

The prodrugs of the sulfur containing biologically active agent are prepared by stirring the appropriate mercapto compound, e.g., methyl-N(2-methyl-3-thiopropionyl)proline with 2–4 equivalents of a compound with the formula:

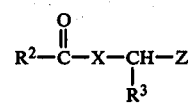

wherein X, $R^2$, and $R^3$ are as above defined and Z is a suitable leaving group, e.g., chloride, bromide, iodide, dimethylamine, tosylate, etc., with or without the presence of 2–4 equivalents of a base, e.g., potassim carbonate in a suitable solvent such as acetone, methylethylketone, cyclohexanone, benzene, toluene, tetrahydrofuran, dioxane, dimethylsulfoxide or the like to form a compound having the structural formula:

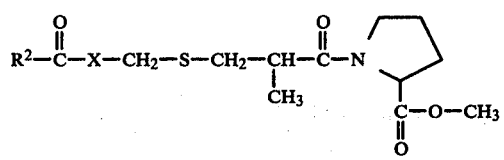

The protective methyl group may be removed by standard methods to produce the sulfur protected antihypertensive agent or the carboxyl protected derivative may be used as the methyl ester.

As in the case of N-(2-methyl-3-thiopropionyl)proline, the biologically active mercapto containing agents may also have other reactive groups, e.g., alcohol, carboxyl, amino, which must be protected during the course of the reaction with

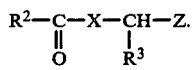

The chemistry of protecting these groups is well known to one skilled in the art. The N-protected or O-protected compounds, thus, not only are useful intermediates, but are also useful final products, also demonstrating the utility of the patent drug species.

The reaction with

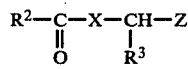

may be run at a temperature of from $-20°$ C. to the boiling point of the solvent. The course of the reaction is usually monitored by thin layer chromatography or nuclear magnetic resonance spectroscopy or other convenient method.

The reactant

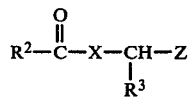

wherein X is O, S, $NR^5$, is prepared thus:

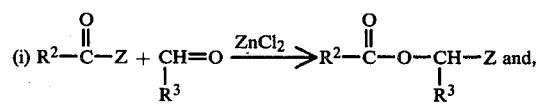

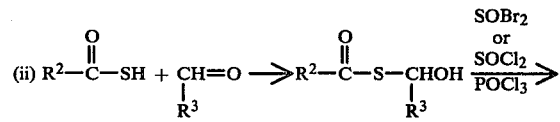

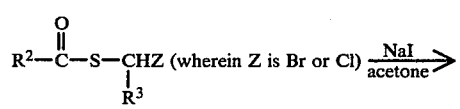

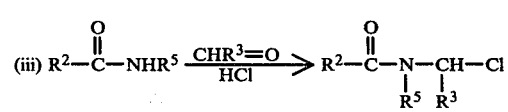

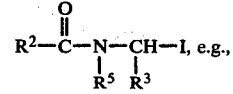

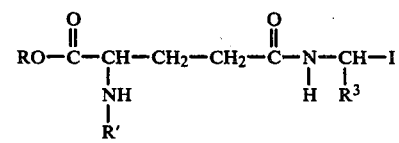

wherein R and R' are protective groups, e.g.,
R = $C_6H_5$—$CH_2$— and
R' = $C_6H_5$—$CH_2$—O—CO—     or

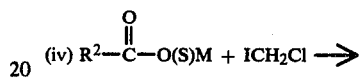

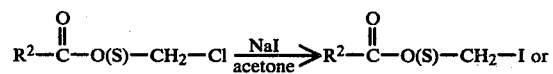

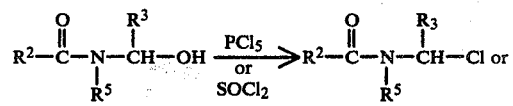

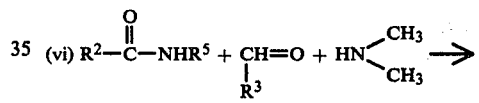

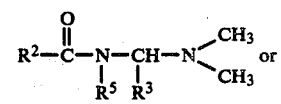

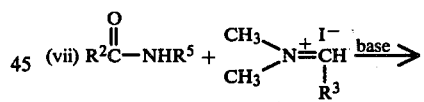

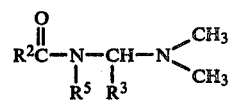

Several representative synthetic schemes, thus, would include:

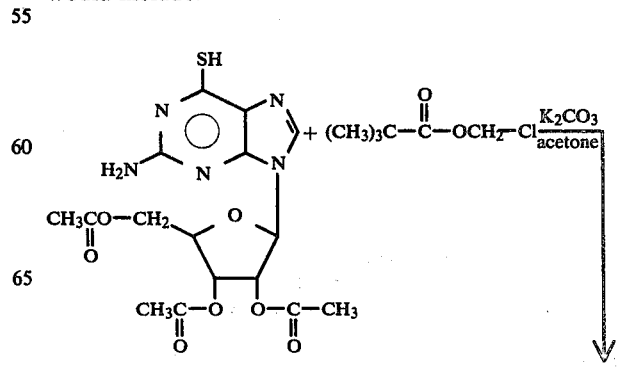

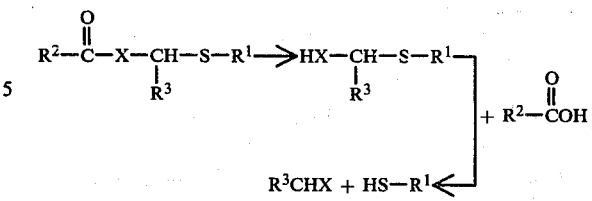

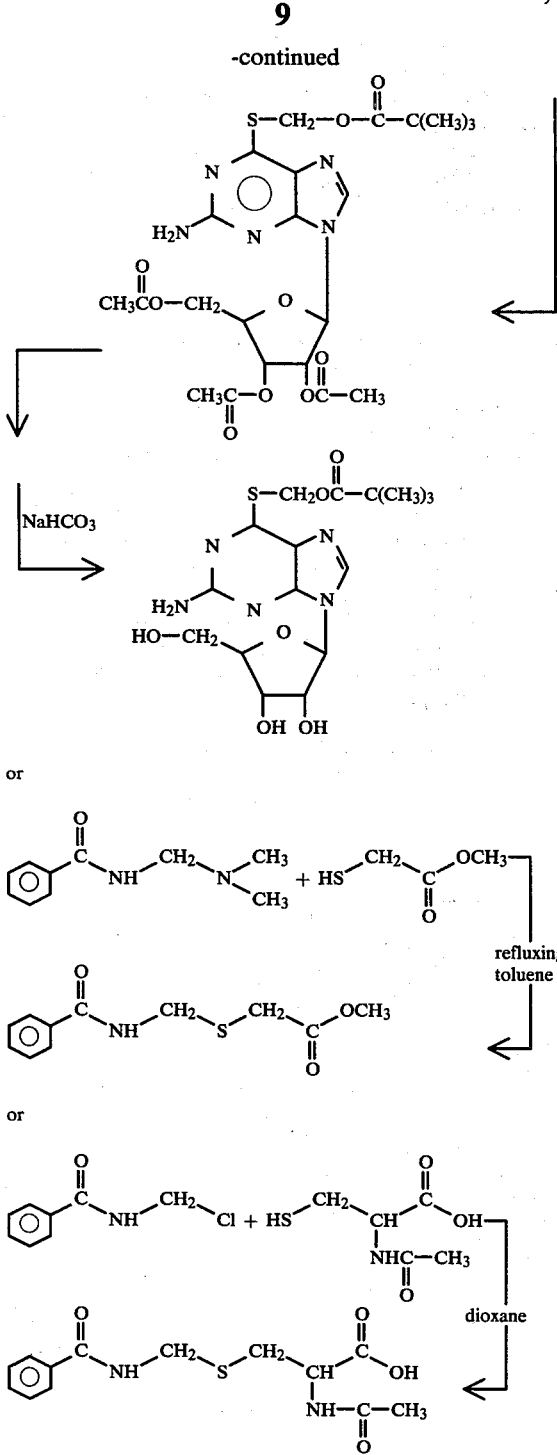

While all of the compounds according to the invention are characterized by good lipid solubility and high bioavailability, are quite stable to both air and light, and are more immune to chemical attack by those agents which are conventionally used in pharmaceutical preparations, the same are nonetheless facilely chemically and/or enzymatically metabolized/hydrolyzed at their therapeutic sites of action, i.e., upon administration are cleaved into the known and proven parent drug molecule, e.g., N-acetylcysteine, per se, as well as into various non-toxic products of metabolism/hydrolysis, according to the following general scheme:

It will be appreciated that it is a critical feature of the present invention that the ether sulfur and the X function comprising the acyl-X-methylthioether moiety of the subject prodrug compounds be separated by but a single carbon atom or methylene bridge. Otherwise, e.g., if the "methylene" linkage were ethylene or higher alkylene, such compounds would not be subject to the aforesaid chemical and/or enzymatic metabolism/hydrolysis and would not be facilely cleaved in vivo, into the noted non-toxic products of metabolism/hydrolysis. Hence, such ethylene and higher alkylene congeners are inoperative and not intended herein; indeed, same could not properly be deemed or designated as true "prodrugs."

While all of the compounds encompassed within the aforesaid generic formula (I) meet applicants' criteria, nevertheless certain compounds remain preferred, namely, the pivalyloxymethyl, hexanoyloxymethyl, heptanoyloxymethyl, octanoyloxymethyl, n-dodecanoyloxymethyl, n-tetradecanoyloxymethyl, n-hexadecanoyloxymethyl, acetyloxymethyl, pentanoyloxymethyl, benzoyloxymethyl, benzoyloxybenzyl, propionyloxymethyl, butyryloxymethyl, benzoylaminomethyl, pivalylthiomethyl and dimethylaminoacetylaminomethyl derivatives of 6-thio guanosine, 6 mercaptopurine, 6-mercapto purine riboside, thopental, N-(2-methyl-3-thio-propionyl) proline and its esters and amides and N-acetyl cysteine.

In order to further illustrate the present invention and the advantages thereof, the following specific examples are given, it being understood that same are intended only as illustrative and in nowise limitative.

EXAMPLE 1

The preparation of 9-β-D-Ribofuranosyl-2-amino-6-pivalyloxymethyl-thio-9H-purine 2',3',5'-triacetate To a solution of chloromethyl pivalate (106 mg) in (15 ml) sodium iodide (130 mg) was added and then stirred protected from light for 35 min. The supernatant was decanted from the precipitated sodium chloride and added to a solution of thioguanosine triacetate (250 mg) in acetone (25 ml). After adding potassium carbonate (1 g), the reaction mixture was stirred for 69 hours. The suspended solid was then filtered off and washed with acetone. The filtrate was evaporated to dryness. The residue taken in ether was washed three times with water, dried over sodium sulfate and evaporated. The residue was purified by chromatography over silica gel (12.5 g). Elution with chloroform-ethyl acetate (1:1) gave the pure pivalyloxy derivative 82 mg (57.4%) as a foam on vacuum drying. IR (film) 3380, 3490, 1738, 1593, 1562, 1233, 1130, 910, 755 cm$^{-1}$, NMR (CDCl$_3$) δ 1.15 (9H, s, t-Bu), 2.05 (3H, s, Ac), 2.08 (3H, s, Ac), 2.13 (3H, s, Ae), 4.41 (3H, s, CH$_2$OAc+4'-H), 5.20 (2H, s, NH$_2$), 5.80 (1H, broad, 3'-H̲), 5.93 (2H, s, SCH$_2$), 5.96

(1H, t, 2'-H), 6.0 (1H, d, 1'-H) and 7.8 (1H, s, aromatic), MS (m/e) 539 (M+).

EXAMPLE 2

The Preparation of 9-β-D-Ribofuranosyl-6-pivalyloxymethylthio-9H-purine 2',3',5'-triacetate Chloromethyl pivalate (112 mg) in acetone (10 ml) was stirred with sodium iodide (135 mg) in the absence of light for 40 min. The clear solution was decanted into a solution of 9-β-D-ribofuranosyl-6-thio-9H-purine 2',3',5'-triacetate (254 mg) in 30 ml of acetone. Potassium carbonate (1 g) was added and stirred protected from light. When the reaction was complete, the reaction mixture was filtered and the filtrate was evaporated. The residue was dissolved in ethyl acetate and washed three times with water. The EtOAc extract was dried over $Na_2SO_4$ and evaporated to yield a residue weighing 350 mg which was contaminated with traces of pivalyloxymethyl halides. It was filtered through silica gel (12.5 g) in EtOAc. The pure compound was obtained as a pale white waxy solid 296 mg (91.3%). IR (film) 1755, 1575, 1232, 1133 cm$^1-$. NMR (CDCl$_3$) δ1.10 (9H, s, butyl), 2.03 (3H, s, Ac), 2.06 (3H, s, Ac), 2.15 (3H, s, Ac), 4.43 (3H, CH$_2$OAc+4'-H), 5.70 (1H, m, 3'-H), 6.0 (1H, k, 2'-H), 6.25 (1H, d, 1'-H), 8.2 (1H, s, aromatic) and 8.76 (1H, aromatic), MS (m/e) 524 (M+).

EXAMPLE 3

The Preparation of 6-(Benzamidomethylthio)purine

Chloromethylbenzamide (55.71 mg, 0.328 mmol) and 6-mercaptopurine (50 mg, 0.328 mmol) were dissolved in 1.5 ml of dry DMSO-d$_6$ to give a clear yellow solution. The progress of the reaction was followed by monitoring changes in the NMR spectrum. The doublet at 5.42, due to chloromethylbenzamide, had completely disappeared after 10 hours and a new doublet at 5.83 indicated the presence of the benzamidomethylthio moiety. Chloroform was added which caused a yellow gum to precipitate which was washed several times with chloroform and crystallized from methanol: mp 197°–200° C.; IR (KBR) 1720 cm$^{-1}$; NMR (pyridin-d$_5$) δ8.39–7.35 (m, 5, aryl), 5.99 (d, 2, —SCH$_2$NH—); MS m/e 285 (M+).

Anal. Calcd. for $C_{13}H_{11}N_5SO$ (285.18): C, 54.74; H, 3.85; N, 24.54. Found: C, 54.46; H, 3.59; N, 24.20.

EXAMPLE 4

The Preparation of N-acetyl-S-benzamidomethyl-L-cysteine

N-acetyl-L-cysteine (0.5 g, 3.06 mmol) was dissolved in 50 ml of dry dioxane. Chloromethyl benzamide (0.52 g, 3.06 mmol) was added and the colorless solution was stirred at 25° C. for 18 hours. The dioxane was evaporated under vacuum with minimal amount of heating to give a colorless oil: NMR (CDCl$_3$+DMSO) δ8.05–7.38 (m, 5, aryl), 4.58 (d, 2, —SCH$_2$NH—), 2.01 (s, 3, —CH$_3$).

EXAMPLE 5

The Preparation of Methyl-S-(benzamidomethyl)thioglycolate

Methyl thioglycolate (2 g, 18.84 mmol) and chloromethylbenzamide (3.2 g, 18.84 mmol) was dissolved in 60 ml of dry toluene, and the clear solution was stirred for 18 hours at 25° C. under nitrogen at which time a TLC (10% EtOAc/CH$_2$Cl$_2$) showed that the reaction was complete. Solid materials were removed by filtration and the toluene was evaporated to give a pale yellow oil. Purification on silica gel (10% EtOAc/CH$_2$Cl$_2$) yielded a colorless oil that solidified on standing: mp 65°–68° C.; IR (KBr) 3280, 1730, 1620 cm$^{-1}$; NMR (CDCl$_3$) δ7.98–7.25 (m, 5, aryl), 4.77 (d, 2, —SCH$_2$NH—), 3.77 (s, 3, —OCH$_3$), 3.43 (s, 2, —SCH$_2$-C=O).

EXAMPLE 6

The Preparation of Methyl-S-(benzamidomethyl)thioglycolate from N,N-Dimethylaminomethyl-benzamide N,N-Dimethylaminomethyl-benzamide (2 g, 18.84 mmol) and methyl thioglycolate (3.36 g, 18.84 mmol) were dissolved in dry toluene and the solution was refluxed for 2 days under nitrogen. Upon cooling, some methylenebisbenzamide crystallized out of solution and it was removed by filtration. Evaporation of the solvent yielded an oil that crystallized on standing: mp 65°–68° C.; IR (KBr) 3280, 1730, 1620 cm$^{-1}$; NMR (CDCl$_3$) δ7.98–7.25 (m, 5, aryl), 4.77 (d, 2, —SCH$_2$NH—), 3.77 (s, 3, —OCH$_3$), 3.43 (s, 2, —SCH$_2$C=O).

The following compounds are also prepared utilizing those techniques above outlined:

TABLE I $$R^2-\overset{O}{\underset{}{\overset{\|}{C}}}-X-\underset{R^3}{\overset{}{\text{CH}}}-S-R^1$$

| R$^1$—S residue | R$^2$ | R$^3$ | X |
|---|---|---|---|
| N—Acetyl cysteine | (CH$_3$)$_3$C— | H | O |
| N—Acetyl cysteine | (CH$_3$)$_3$C— | CH$_3$ | S |
| Cysteine methyl ester | (CH$_3$)$_3$C— | C$_2$H$_5$ | O |
| Cysteine methyl ester | C$_6$H$_5$ | H | NH |
| Penicillamine | CH$_3$(CH$_2$)$_5$— | H | O |
| Penicillamine | 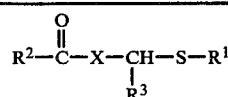 | H | O |
| Dimercaprol | C$_{12}$H$_{25}$ | H | S |
| Dimercaprol | (CH$_3$)$_3$C— | CH$_3$ | O |
| N(2-methyl-3-thio-propionyl)-proline | (CH$_3$)$_3$C— | H | O |
| N(2-methyl-3-thio-propionyl)-proline | C$_6$H$_5$ | CH$_3$ | NH |
| N(2-methyl-3-thio-propionyl)-proline | CH$_3$(CH$_2$)$_5$— | H | S |
| N(2-methyl-3-thio-propionyl)-proline | 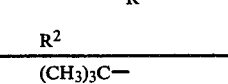 | CF$_3$ | S |
| N(2-methyl-3-thio-propionyl)-proline ethyl ester | (CH$_3$)$_3$C— | CH$_3$ | O |
| N(2-methyl-3-thio-propionyl)-proline ethyl ester | C$_5$H$_{11}$ | CCl$_3$ | O |
| 2-thio pyridine N—oxide | —CH$_2$—NH$_2$ | CH$_3$ | O |
| 2-thio pyridine N—oxide | 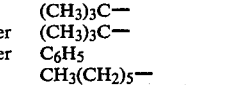 | H | O |
| 6-mercapto purine | (CH$_3$)$_3$C— | CH$_3$ | O |

TABLE I-continued $$R^2-\overset{O}{\overset{\|}{C}}-X-\overset{R^3}{\underset{|}{CH}}-S-R^1$$

| $R^1$—S residue | $R^2$ | $R^3$ | X |
|---|---|---|---|
| 6-mercapto purine | —CH$_2$CH$_2$—CH—COOH<br>                            \|<br>                            NH$_2$ | H | NH |
| 6-mercapto purine riboside | (CH$_3$)$_3$C | H | O |
| 6-mercapto purine riboside | CH$_3$(CH$_2$)$_3$— | CH$_3$ | S |
| 6-thioguanosine | (CH$_3$)$_3$C | H | O |
| 6-thioguanosine | C$_6$H$_5$ | CH$_3$ | NCH$_3$ |
| 6-thioguanosine | CH$_3$ | H | O |
| 6-thioguanosine | CH$_3$(CH$_2$)$_{16}$ | H | O |
| Thiopental | (CH$_3$)$_3$C | H | O |
| Thiopental | CH$_3$(CH$_2$)$_5$— | CH$_3$ | S |
| 2-Thiouracil | C$_6$H$_5$ | C$_2$H$_5$ | S |
| 2-Thiouracil | (phenyl ring) | H | O |
| Methimazole | CH$_3$ | CF$_3$ | O |

EXAMPLE 7

The Preparation of S-(3-Phthalidyl)-N-acetyl-L-cysteine

To 1.63 g (0.01 mole) of N-acetyl-L-cysteine dissolved in 20 ml of hot acetonitrile was added 1.5 g (0.01 mole) of 2-phthalaldehydic acid. The solution was heated at reflux for 2 hr then concentrated to give a yellow gum which was triturated with THF-ether, 10:60. The insoluble gummy oil was dried in vacuo to give the desired product: $^1$H NMR (CDCl$_3$) 10.83 (broad s, 1, CO$_2$H), 8.0–7.4 (m, 4, aromatic H), 7.4–7.0 (broad d, 1, —NHCOCH$_3$), 6.63 (d, 1, C$\overline{O_2}$CHOS), 5.05–4.65 (m, 1, C$\overline{H}$ONHCOCH$_3$), 3.6–2.8 (m, 2, C$\overline{H_3}$S) and 2.1 (s, 3, C$\overline{H_3}$S) and 2.1 (s, 3, CH$_3$—CON).

EXAMPLE 8

The preparation of 6-Pivalyloxymethylthio-3-pivalyloxymethylpurine and 6-Pivalyloxymethylthio-9-pivalyloxymethylpurine To 2.0 g (0.01176 mole) of 2-mercaptopurine hydrate suspended in 10 ml of CH$_2$Cl$_2$ was added 6 ml of triethylamine. After 10 min 5.28 g (0.0351 mole) of pivalyoxymethyl chloride was added to the suspension which was then stirred at room temperature for 2 days. The suspension was dissolved in 100 ml of CH$_2$Cl$_2$. The CH$_2$Cl$_2$ solution was washed with 25 ml of 2 N HCl and 25 ml of water, then it was dried over Na$_2$SO$_4$ and conc. in vacuo to give a yellow gum. The gum was triturated with 50 ml of ether and filtered. The residue (0.48 g, mp 193°–197°, 11% yield) was 6-pivalyloxymethylthio-3-pivalyloxymethylpurine: analytical sample (66 mg from 100 mg in CH$_2$Cl$_2$— ether, 1:5 ml) mp 198°–199°; IR (KBr) 1735 cm$^{-1}$ (s) (C=O); $^1$H NMR (CDCl$_3$) δ8.5 (s, 1, N=CH—N), 8.17 (s, 1, N=CH—N), 6.37 (s, 2, NCH$_2$O$_2\overline{C}$), 6.01 (s, 2, S—CH$_2$O$_2\overline{C}$) and 1.2 (s, 19, (C$\overline{H_3}$)$_3$—C); TLC (silica gel, ether) R$_f$0.0.

Anal. Calcd for C$_{17}$H$_{24}$N$_4$O$_4$S: C, 53.66; H, 6.36; N, 14.73. Found: C, 53.68; H, 6.30; N, 14.80.

The ether filtrate above was chromatographed on silica gel using ether as the eluent to give 2.70 g of a colorless viscous oil which was triturated with petroleum ether bp 30°–75° to give 1.64 g (Mp 53°–55°, 36% yield) of 6-pivalyloxymethylthio-9-pivalyoxymethylpurine as white crystals: IR (KBr) 1735 cm$^{-1}$ (s) (C=O); $^1$H NMR (CDCl$_1$) δ8.83 (s, 1, N=CH=N), 6.18 (s, 2, N—CH$_2$O$_2$C), 6.03 (s, 2, S—CH$_2$O$_2\overline{C}$), 1.18 (s, 18, (s, 18, (C$\overline{H_3}$)$_3$C); TLC (silica gel, ether) R$_f$0.52.

Anal. Calcd for C$_{17}$H$_{24}$N$_4$O$_4$S: C, 53.66; H, 6.36; N, 14.73. Found: C, 53.88; H, 6.51; N, 14.80.

When the petroleum ether filtrate above was concentrated an addition 0.25 g (mp 51°–54°, 6% yield) of the 6,9-substituted product was obtained.

EXAMPLE 9

The Preparation of 2-Pivalyloxymethylthiopyrimidine

A suspension of 1.1 g (0.01 mole) of 1-mercaptopyrimidine in 20 ml of CH$_2$Cl$_2$ was allowed to react with 1.05 g (0.01 mole) of triethylamine for 5 min. Then the suspension was treated with 1.5 g (0.01 mole) of pivalyloxymethyl chloride for 0.5 hr. Then more triethylamine (2.0 g) was added. After 0.5 hr a clear solution was obtained which almost immediately started to form a precipitate. The suspension was stirred at room temperature overnight. The suspension was dissolved in CH$_2$Cl$_2$ (100 ml). The CH$_2$Cl$_2$ solution was washed with 10% HCl (25 ml) and water (25 ml), then dried over Na$_2$SO$_4$ and conc. to give a yellow oil (1.45 g). The oil was chromatographed on silica gel using ether as the eluent to give 1.1 g (49% yield) of the desired pyrimidine as a colorless oil: IR (neat) 1735 cm$^{-1}$ (s) (C=O); $^1$H NMR (CDCl$_3$) δ8.73–8.5 (m, 2, CH—N), 7.2–6.93 (m, 1, C—CH=C), 5.8 (s, 2, CO$_2$C$\overline{H_2}$) and 1.17 (s, 9, (CH$_3$)$_3$—C); TLC (silica gel, ether) R$_f$0.46. (No starting material (R$_f$0.0) could be seen).

EXAMPLE 10

The Preparation of 1-Methyl-2-pivalyloxymethylthioimidazole

To 1.53 g (0.01 mole) of pivalyloxymethyl chloride dissolved in 30 ml of THF was added 1.14 g (0.01 mole) of 1-methyl-2-mercaptoimidazole. The clear yellow solution that resulted was stirred at room temperature overnight. The solution was concentrated to give a glass which was triturated twice with 100 ml of ether. The suspension was filtered and the residue was dried to give 1.85 g (mp 128°–132°, 67% yield) of the desired product as its hydrochloride. IR (KBr) 2800–2200 cm$^{-1}$; (broad, s) (N$^+$H), 1730 cm$^{-1}$ (s) (C=O) and 1870 and 1820 cm$^{-1}$; $^1$H NMR (CDCl$_3$) δ7.60 (broad s, 2, N—CH=CH—N), 5.85 (s, 2, CO$_2$CH$_2$S), 3.57 (s, 3, N—C$\overline{H_3}$) and 1.18 (s, 9, (CH$_3$)$_3$C).

Anal. Calcd for C$_{10}$H$_{17}$C$\overline{l}$N$_2$O$_2$S: C, 45.36; H, 6.47; N, 10.58. Found: C, 45.28; H, 6.53; N, 10.60.

A portion of the hydrochloride (0.5 g) was suspended in CH$_2$Cl$_2$ (50 ml) and neutralized with 0.2 g of NaOH dissolved in 5 ml of water by vigorously shaking the byphasic mixture until all the solid had dissolved. The CH$_2$Cl$_2$ solution was separated dried over Na$_2$SO$_4$ and evaporated to give the desired product as a clear, light yellow oil: IR (neat) 1730 cm$^{-1}$ (s) (C=O); $^1$H NMR (CDCl$_3$) δ7.13 (sharp m, 1, N—CH=CH—N), 6.97 (sharp m, 1, N—CH=CHN), 5.47 (s, $\overline{2}$, CO$_2\overline{C}$H$_2$S), 3.67 (s, 3, N—CH$_3$) and 1.15 (s, 9, (CH$_3$)$_3$C); TLC (silica gel, ether) R$_f$0.26; mass spectrum (m/e), 228 (M$^+$).

From the foregoing, it will be appreciated that the prodrug derivatives according to the inventor exhibit all of the biological and therapeutic activity of their "parent" mercapto compounds, whether for the treatment of hypertension, cancer, metal poisoning, excess mucus, psoriasis, hyperthyroidism or pain (general anesthesia), or any other disease state or condition responsive to active agents, while at the same time being characterized by enhanced bioavailability and physiological availability, enhanced resistance to deterioration by air and light and to chemical attack, and even the ability to elicit the same pharmacological response as the parent drug form, but at lower dosages.

The dose of the prodrug administered, whether orally, topically, inhalation spray or mist, intravenous or ophthalmic solution, ointment, or the like, and whether a single dose or a daily dose, will, of course, vary with the needs of the individual. However, the dosage administered is not subject to definite bounds, but will usually be an effective amount, or the equivalent on a molar basis of the pharmacologically active form produced upon the metabolic release of the active drug to achieve its desired and physiological effect. See *Physicians' Desk Reference*, 31 (1977). Moreover, for any of the broad spectrum of dosage forms into which the subject produced can be formulated see *Remington's Pharmaceutical Sciences*, 14th Edition (1970).

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A compound selected from the group consisting of those having (i) the structural formula I:

$$R^2-\overset{O}{\underset{\|}{C}}-X-\underset{\underset{R^3}{|}}{CH}-S-R^1$$

wherein
X is O, S or $NR^5$;
$R^1S$ is the deprotonated residue of a biologically active agent $R^1SH$ which is a thiopurine derivative selected from the group consisting of 6-mercaptopurine and a sugar and/or an acetate derivative thereof selected from a group consisting of 6-mercaptopurineriboside and 9-$\beta$-D-ribofuranosyl-6-thio-9H-purine-2′,3′,5′-triacetate;
$R^2$ is
(a) straight or branched chain alkyl having from 1 to 20 carbon atoms;
(b) aryl having from 6 to 10 carbon atoms;
(c) cycloalkyl having from 3 to 8 carbon atoms;
(d) alkenyl having from 2–6 carbon atoms;
(e) cycloalkenyl having from 5 to 8 carbon atoms;
(f) carboxyalkyl or alkanoyloxyalkyl having from 2–6 carbon atoms;
$R^3$ is
(a) hydrogen;
(b) $R^2$;
(c) lower alkanoyl having from 2–6 carbon atoms; or
(d) haloloweralkyl having from 1–6 carbon atoms;
$R^5$ is hydrogen or lower alkyl having 1–6 carbon atoms;

(ii) prodrugs having the structural formula (I) wherein $$R^2-\overset{O}{\underset{\|}{C}}-$$

is the residue of a naturally occurring protein amino acid, the residue of a N-substituted naturally occurring amino acid, which N-substituent is $C_{1-6}$ alkyl or an amino acid protective group cleavable via hydrogenolysis or hydrolysis selected from the group consisting of formyl, benzyloxy, carbonyl, and t-butyloxycarbonyl, or the residue of an N,N-lowerdialkyl or $C_4$–$C_7$ cycloalkylamino acids; and
(iii) a non-toxic, pharmaceutically acceptable salt thereof.

2. A compound as defined in claim 1, wherein $R^2$ is
(a) straight or branched chain $C_{1-12}$ alkyl;
(b) phenyl;
(c) $C_{3-8}$ cycloalkyl;
(d) $C_{2-6}$ alkenyl;
(e) $C_{5-8}$ cycloalkenyl;
(f) $C_{2-6}$ alkynyl;
$R^3$ is
(a) hydrogen;
(b) $C_{1-6}$ alkyl;
(c) halo $C_{1-6}$ alkyl;
(d) trichloromethyl; or
(e) trifluoromethyl.

3. A compound of claim 2 wherein $R^1S$ is the residue of a 6-mercaptopurine derivative or sugar and/or an acetate derivative thereof selected from a group consisting of 6-mercaptopurine riboside; and 9-$\beta$-ribofuranosyl-6-thio-9H-purine-2′,3′,5′-triacetate.

4. The compound of claim 3 wherein $R^2$ is
(a) phenyl; or
(b) straight and branched chain alkyl having from 1 to 6 carbon atoms.

5. The compound of claim 4 wherein $R^2$ is
(a) phenyl; or
(b) t-butyl.

6. The compound of claim 4 wherein X is $NR^5$; $R^5$ is hydrogen or methyl; and $R^3$ is hydrogen or methyl.

7. The compound of claim 3 wherein $R^1S$ is the residue of 6-mercaptopurine; $R^2$ is t-butyl; $R^3$ is methyl and X is O.

8. The compound of claim 3 wherein $R^1S$ is the residue of 6-mercaptopurine; $R^2$ is $$CH_2CH_2-\underset{\underset{NH_2}{|}}{CH}COOH;$$

$R^3$ is hydrogen; and
X is NH.

9. The compound of claim 3 wherein $R^1S$ is the residue of 6-mercaptopurine riboside; $R^2$ is t-butyl; $R^3$ is H; and X is O or S.

10. The compound of claim 3 which is
(a) 6-(benzamidomethylthio)purine;
(b) 6-pivalyloxymethylthio-3-pivalyloxymethylpurine; or
(c) 6-pivolyloxymethylthio-9-pivalyloxymethylpurine;
(d) 9-β-D-ribofuranosyl-2-amino-6-pivalyloxymethylthio-9H-purine-2',3',5'-triacetate;
(e) 9-β-D-ribofuranosyl-6-pivolyloxymethylthio-9H-purine-2',3',5'-triacetate.

11. A therapeutically effective composition of matter comprising an effective amount of a compound as defined by claim 1, and a pharmaceutically effective carrier therefor.

12. The method of eliciting the corresponding therapeutic response in a warm-blooded animal, which comprises administering to such animal an effective amount of a compound as defined by claim 1.

* * * * *